United States Patent
Gupta et al.

(10) Patent No.: US 11,013,395 B2
(45) Date of Patent: May 25, 2021

(54) ENDOSCOPE RESTRAINT

(71) Applicant: NEW YORK UNIVERSITY, New York, NY (US)

(72) Inventors: Nikhil Gupta, Ossining, NY (US); Farid Razavi, Allentown, PA (US)

(73) Assignee: NEW YORK UNIVERSITY, New York, NY (US)

(*) Notice: Subject to any disclaimer, the term of this patent is extended or adjusted under 35 U.S.C. 154(b) by 384 days.

(21) Appl. No.: 15/708,387

(22) Filed: Sep. 19, 2017

(65) Prior Publication Data

US 2018/0078115 A1 Mar. 22, 2018

Related U.S. Application Data

(60) Provisional application No. 62/397,253, filed on Sep. 20, 2016.

(51) Int. Cl.
| | | |
|---|---|---|
| *A61B 1/00* | (2006.01) | |
| *A61B 1/005* | (2006.01) | |
| *A61B 1/06* | (2006.01) | |
| *A61B 1/31* | (2006.01) | |

(52) U.S. Cl.
CPC .......... *A61B 1/0014* (2013.01); *A61B 1/0052* (2013.01); *A61B 1/00066* (2013.01); *A61B 1/00128* (2013.01); *A61B 1/00149* (2013.01); *A61B 1/06* (2013.01); *A61B 1/31* (2013.01)

(58) Field of Classification Search
CPC .............. A61B 1/0014; A61B 1/00066; A61B 1/00128; A61B 1/0052; A61B 1/00147

See application file for complete search history.

(56) References Cited

U.S. PATENT DOCUMENTS

| | | | | |
|---|---|---|---|---|
| 5,797,835 A | * | 8/1998 | Green | A61B 17/3401 600/106 |
| 6,210,330 B1 | * | 4/2001 | Tepper | A61B 17/4241 600/439 |
| 2003/0216613 A1 | * | 11/2003 | Suzuki | A61B 17/0469 600/104 |
| 2006/0020213 A1 | * | 1/2006 | Whitman | A61B 1/05 600/478 |
| 2008/0294117 A1 | * | 11/2008 | Ware | A61M 5/1418 604/174 |
| 2011/0152609 A1 | * | 6/2011 | Trusty | A61B 1/00149 600/102 |
| 2012/0149984 A1 | * | 6/2012 | Reilly | A61B 1/00149 600/121 |
| 2014/0200568 A1 | * | 7/2014 | Sharma | A61B 5/1076 606/27 |

(Continued)

*Primary Examiner* — Timothy J Neal
*Assistant Examiner* — William B Chou
(74) *Attorney, Agent, or Firm* — Foley & Lardner LLP

(57) ABSTRACT

An endoscope restraining system for restraining motion of an endoscope tube includes an attachment portion configured to attach the endoscope restraining system to a surface, a flexible tube coupled to the attachment portion at a proximal end of the flexible tube, a base plate coupled to a distal end of the flexible tube, and an endoscope restraint removably connected to the base plate. The endoscope restraint includes a plurality of supports configured to receive the endoscope tube to prevent changes in a torque position, degree of insertion, and lateral movement of the endoscope tube.

17 Claims, 18 Drawing Sheets

(56) References Cited

U.S. PATENT DOCUMENTS

| | | | | |
|---|---|---|---|---|
| 2014/0316204 A1* | 10/2014 | Ofir | ............... | A61B 1/00131 |
| | | | | 600/158 |
| 2016/0324412 A1* | 11/2016 | Hassidov | ........... | A61B 1/00112 |
| 2017/0209022 A1* | 7/2017 | Molnar | ............ | A61M 16/0465 |

* cited by examiner

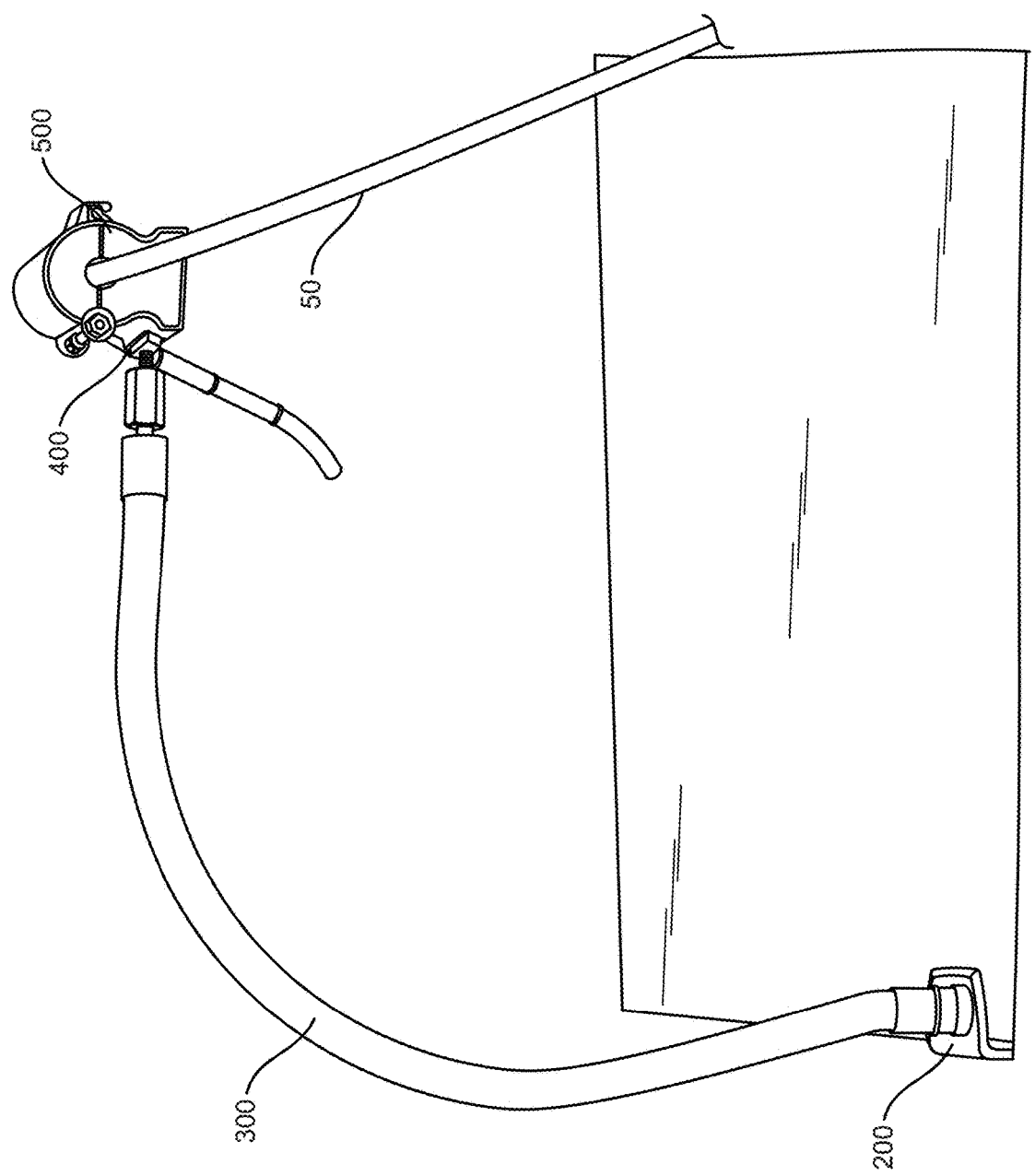

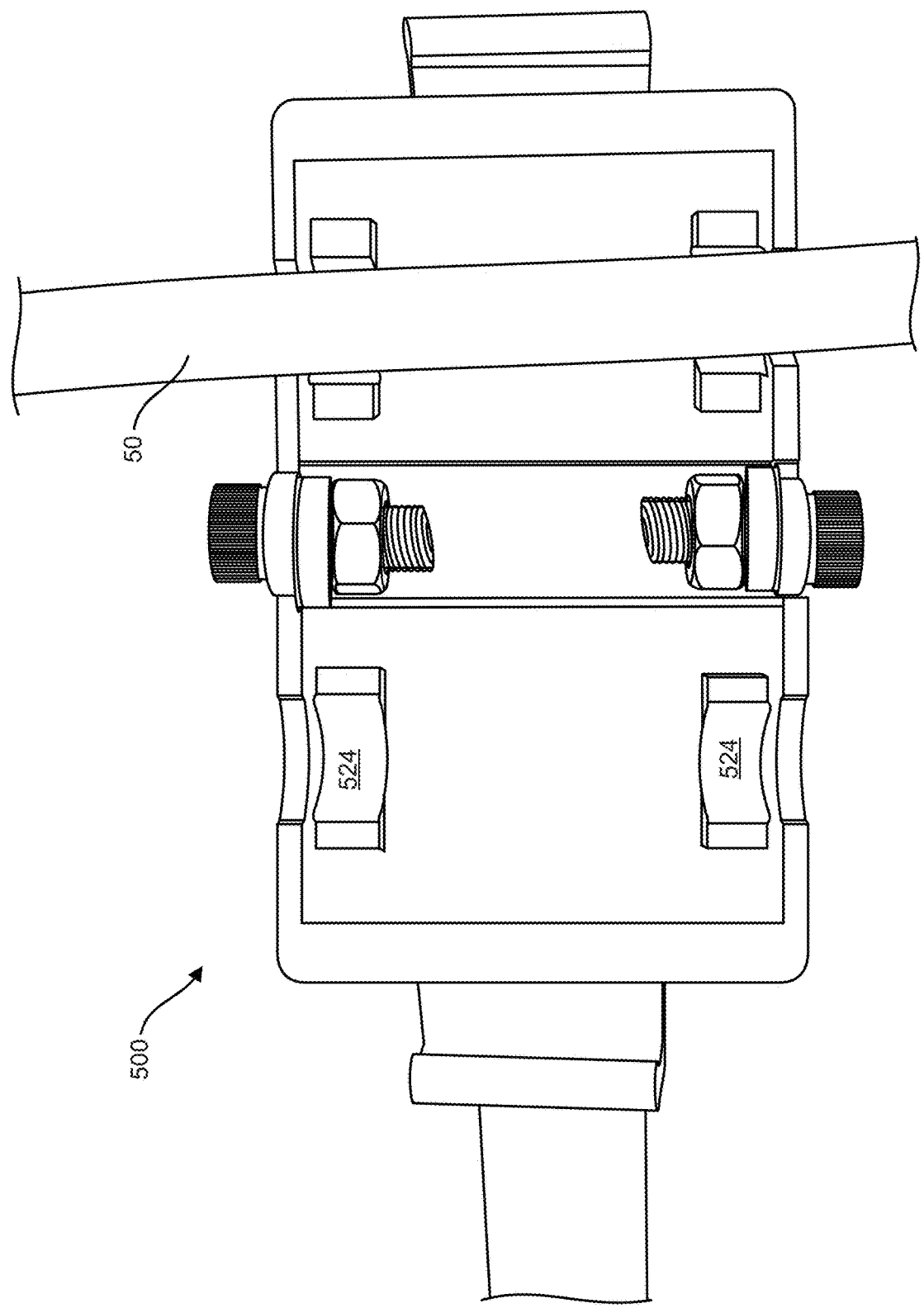

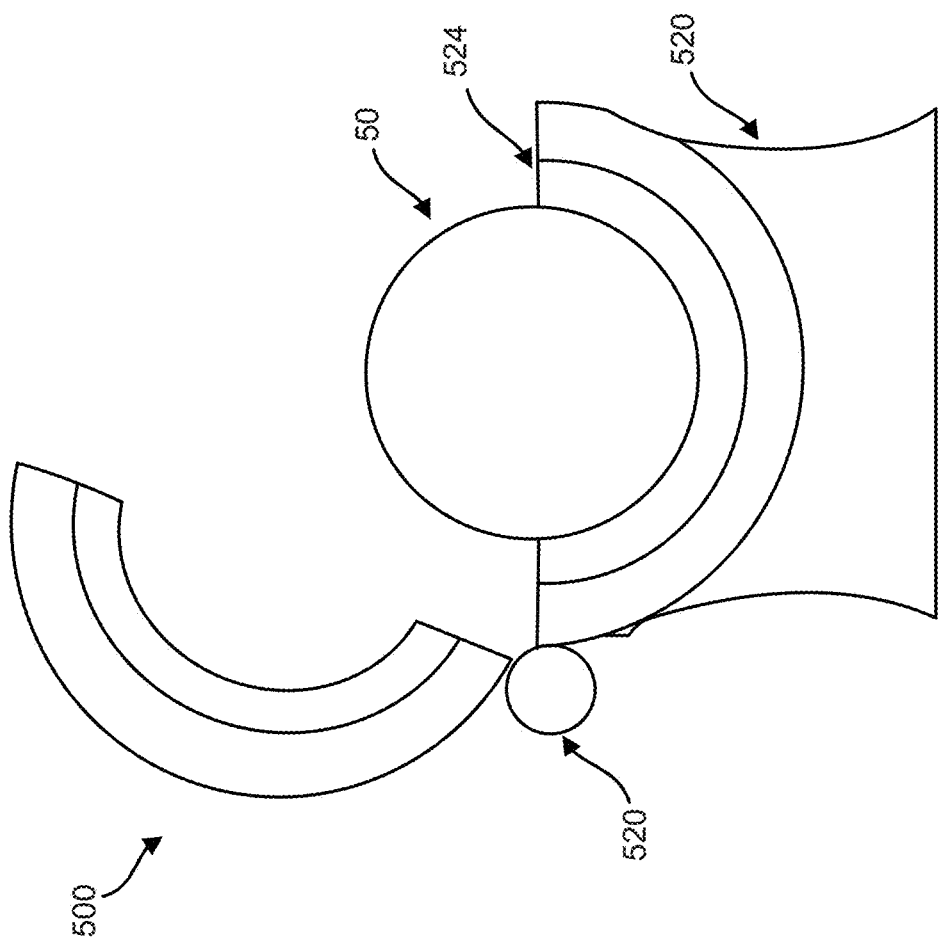

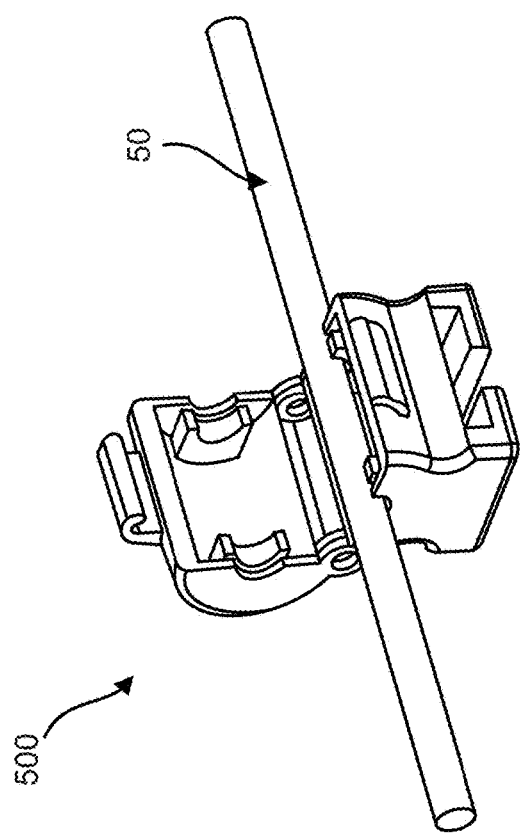
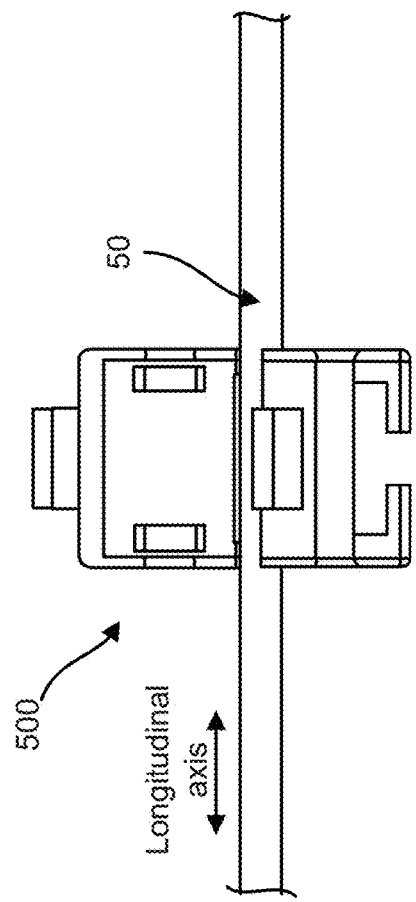

FIG. 20 Maximum equivalent stress vs. silicone rubber Young's Modulus.

ENDOSCOPE RESTRAINT

CROSS-REFERENCE TO RELATED APPLICATIONS

This application claims the benefit of and priority to U.S. Provisional Patent Application No. 62/397,253 filed on Sep. 20, 2016, the entire disclosure of which is incorporated by reference herein.

TECHNICAL FIELD

The present disclosure relates generally to an endoscope. More specifically, the present disclosure relates to an endoscope restraint configured to grasp an endoscope tube to prevent changes in the torque position (clockwise/counter-clockwise direction), degree of insertion (forward/backwards direction), and lateral movement of the endoscope tube.

BACKGROUND

An endoscope includes an approximately four-foot long, flexible tube about the thickness of a finger with a camera and a source of light at its tip. The tip of the endoscope is inserted into the anus and then is advanced slowly, under visual control, into the rectum and through the colon usually as far as the cecum, which is the first part of the colon. This is far from ideal as minor movements or loss of torque, often leading to adverse outcomes including incomplete polyp resection, colonic injury, and acute perforation, commonly jeopardizes scope position.

Referring to FIG. 1, an endoscope 100 generally includes a supply plug 10, an umbilical cord 20, a control head 30, an insertion shaft 40, and an endoscope tube 50. The supply plug 10 is located at one end of the umbilical cord 20 and includes a plurality of connectors 11. The connectors 11 are configured to connect the endoscope 100 to a plurality of external elements, including, but not limited to a light guide, an air supply, a water bottle and suction, and an air vent. The umbilical cord 20 connects the supply plug 10 to the control head 30, which is attached to the other end of the umbilical cord 20. The control head 30 is provided between the umbilical cord 20 and the insertion shaft 40. The control head 30 includes a plurality of controls for air insufflation, irrigation, and suction. The control head 30 may also include mechanisms for steering the endoscope tube 50 located at a distal end of the endoscope 100. The insertion shaft 40 includes air and water jets, a common port 80 (i.e., a combined suction and biopsy port), and a distal lens or video chip. As used herein, the terms "port" and "channel" are synonymous. The endoscope tube 50 extends from the insertion shaft 40, and has a tip, which houses terminal ends of an illuminating end of a light guide.

A fiber optic endoscope has an eyepiece, while a video endoscope has remote control buttons for a video control unit. In a fiber optic endoscope, light is conducted from the distal lens in the endoscope tube 50 to the eyepiece by bundles of optical glass fibers. In a video endoscope, the image is captured with the video chip in the endoscope tube 50, transmitted electronically, and displayed on a monitor.

The biopsy port 60 is located at an intersection of the insertion shaft 40 and the control head 30. The biopsy port 60 is configured for passing sampling and/or operative instruments down the insertion shaft 40 and the endoscope tube 50 to an internal site to be examined or surgically manipulated. The biopsy port 60 is covered by a biopsy valve 61 configured to close off a proximal opening of the biopsy port 60 and prevent room air from being drawn into a suction port 70 located at a distal end of the control head 30. Opening or completely removing the biopsy valve 61 from the biopsy port opening releases the suction in the biopsy port 60.

The biopsy port 60 converges with the suction port 70 to form a common port 80 that passes down the insertion shaft 40 and terminates at a distal end of the endoscope tube 50. Suction is controlled by a suction valve 31 on the control head 30. The suction valve 31 has two positions: a neutral position and a suction position. When the suction valve 31 is not activated, it automatically assumes a neutral position and blocks suction within the suction port 70 and common port 80. When the endoscopist depresses the suction valve 31, the suction port 70 is opened, creating a negative pressure that draws air or fluid into the terminal end of the common port 80 (located in the endoscope tube 50).

During the performance of upper and lower gastrointestinal endoscopy, the endoscopist faces numerous challenges with one of the most important being endoscope control. The following Table 1 lists examples of the types of procedures that are performed using an endoscope.

TABLE 1

| Types or procedures using endoscope. | | | |
| --- | --- | --- | --- |
| Name of procedure | Name of tool | Area or organ viewed | How endoscope reaches target area |
| Arthroscopy | Arthroscope | Joints | Inserted through a small incision over the area to be viewed |
| Bronchoscopy | Bronchoscope | Trachea (windpipe) and bronchi of the lungs | Inserted through the mouth |
| Colonoscopy | Colonoscope | Entire length of the colon and large intestine | Inserted through the anus |
| Colposcopy | Colposcope | Vagina and cervix | A speculum is inserted into the vagina. The colposcope is placed at the opening of the vagina but does not enter it. |
| Cystoscopy | Cystoscope | Inside of the bladder | Inserted through the urethra |
| Esophagoscopy | Esophagoscope | Esophagus | Inserted through the mouth |
| Gastroscopy | Gastroscope | Stomach and duodenum (beginning of the small intestine) | Inserted through the mouth |

TABLE 1-continued

Types or procedures using endoscope.

| Name of procedure | Name of tool | Area or organ viewed | How endoscope reaches target area |
|---|---|---|---|
| Laparoscopy | Laparoscope | Stomach, liver, or other abdominal organ, including female reproductive organs (uterus, ovaries, fallopian tubes) | Inserted through a small surgical opening in the abdomen |
| Laryngoscopy | Laryngoscope | Larynx (voice box) | Inserted through the mouth |
| Neuroendoscopy | Neuroendoscope | Areas of the brain | Inserted through a small incision in the skull near the area to be viewed |
| Proctoscopy | Proctoscope | Rectum and sigmoid colon | Inserted through the anus |
| Sigmoidoscopy | Sigmoidoscope | Sigmoid colon (bottom part of the colon) | Inserted through the anus |
| Thoracoscopy | Thoracoscope | Pleura covering the lungs and structures covering the heart | Inserted through a small surgical opening in chest |

One example of a procedure performed using an endoscope is a colonoscopy. A colonoscopy is the endoscopic examination of the large bowel and the distal part of the small bowel with a CCD or a fiber optic camera on a flexible tube passed through the anus to investigate the inside of the patient's colon. The main purpose of a colonoscopy is the removal of polyps from the colon. Colonic polypectomy is the removal of colorectal polyps in order to prevent them from turning cancerous. The number of polyps varies from one patient to other and can range from as little as 3-4 to as high as 20-25 in a single patient.

The basic procedure for performing a colonoscopy/polypectomy includes inserting the endoscope tube completely inside the colon and slowly withdrawing the endoscope tube by hand movement. While retracting the endoscope tube, locations of all the possible polyps are identified by inspection. Once a polyp is located, the endoscope tube must be held in its exact position (i.e., preventing lateral, transverse and twisting movement) while the polyp is being removed. The endoscopist often requires a nurse's assistance in holding the endoscope shaft in the exact position, while the endoscopist performs the polypectomy to remove the polyp, as the endoscopist requires both hands to perform the polypectomy. The same process is repeated for all of the polyps present inside the colon, as they are removed one by one while withdrawing the endoscope tube. When the procedure is complete, the endoscope tube is removed from the colon.

The endoscopist performs technically challenging maneuvers during a polypectomy, which require precise control and positioning of the endoscope for effective, complete, and safe resection of adenomatous or malignant tissue. Quite often, an ideal position for polypectomy requires a significant amount of maneuvering along with clockwise or counterclockwise torque of the endoscope shaft. As the endoscopist only has one free hand, he/she must rely on their nurse or technician to hold torque. During the transition of insertion shaft handling from endoscopist to nurse, it happens frequently that the exact position of the end camera is lost and thus, the location of the polyp is lost, since the torque which the nurse provides does not match that previously provided by the endoscopist to hold the insertion shaft in position. This is far from ideal as scope position is commonly jeopardized by minor movements or loss of torque pressure, often leading to adverse outcomes including incomplete polyp resection and acute colonic perforation. In addition, once the position of the polyp is lost, the scope has to be adjusted again, thus causing more discomfort to patient and it becomes tiresome for the endoscopist as well.

During the colonoscopy, it is essential to remove all the prevailing polyps in the colon so as to completely fulfill the purpose of the procedure. Despite significant advances in the field, interval colorectal cancer, cancer detected after a reportedly unremarkable colonoscopy or "complete" polypectomy, remains a significant issue. Incomplete polyp resection is the second leading cause of interval colorectal cancer behind missed polyps, accounting for up to 30% of cases. Potential contributing factors to incomplete resection include poor visibility, challenging location within the colon, and poor scope control. While colonoscopy is generally safe, acute colonic perforation can be a devastating procedural outcome occurring as a result of several factors including blunt force and trauma during tissue resection. Perforation has been reported in up to 0.3% of all screening colonoscopies. When faced with larger or "complex" polyps, generally >2 cm in size, advanced techniques including endoscopic mucosal resection and endoscopic submucosal dissection are necessary with reported perforation rates ranging from 0.2% to 5%. The higher incidence of perforation during polypectomy underscores the need for meticulous scope control to ensure complete and safe resection. As the number of endoscopic procedures continue to grow yearly, with upwards of 55 million endoscopies performed yearly (18.6 million in the USA alone), the issue of safety and efficacy becomes paramount.

A need exists for improved technology, including technology that may address the above problems, namely by providing an endoscope restraint configured to grasp an endoscope tube to prevent changes in the torque position (clockwise/counterclockwise direction), degree of insertion (forward/backwards direction), and lateral movement of the endoscope tube.

SUMMARY

One embodiment relates to an endoscope restraining system for restraining motion of an endoscope tube that includes an attachment portion configured to attach the endoscope restraining system to a surface, a flexible tube coupled to the attachment portion at a proximal end of the flexible tube, a base plate coupled to a distal end of the flexible tube, and an endoscope restraint removably connected to the base plate. The endoscope restraint includes a plurality of supports configured to receive the endoscope tube to prevent changes in a torque position, degree of insertion, and lateral movement of the endoscope tube.

Another embodiment relates to an endoscope restraint for an endoscope tube that includes a housing including an endoscope tube retention portion and a base plate retention portion. The endoscope tube retention portion includes a plurality of supports configured to receive an endoscope tube to prevent changes in a torque position, degree of insertion, and lateral movement of the endoscope tube.

Yet another embodiment relates to a method of restraining motion of an endoscope tube during a surgical procedure. The method includes attaching an endoscope restraining system to a surface, where the endoscope restraining system including a base plate coupled to a distal end of a flexible tube; connecting an endoscope restraint to the base plate; and securing the endoscope tube within the endoscope restraint via a plurality of supports configured to receive the endoscope tube and prevent changes in a torque position, degree of insertion, and lateral movement of the endoscope tube.

BRIEF DESCRIPTION OF THE DRAWINGS

The details of one or more implementations of the subject matter described in this specification are set forth in the accompanying drawings and the description below. Other features and aspects of the subject matter will become apparent from the description, the drawings, and the claims presented herein.

FIG. 4 illustrates a side view of the endoscope restraining system of FIG. 2 attached to a table. In FIG. 4, a flexible tube of the endoscope restraining system is bent such that a base plate of the endoscope restraining system is parallel to the table.

FIG. 10 illustrates another top view of the endoscope restraint of FIG. 7 with an endoscope tube provided in the endoscope restraint.

FIG. 11 is a schematic illustration of a side view of a support included in the endoscope restraint of FIG. 7.

FIG. 12 illustrates the endoscope restraint of FIG. 7 from another perspective.

FIG. 13 illustrates a front view of the endoscope restraint of FIG. 7.

DETAILED DESCRIPTION OF VARIOUS EMBODIMENTS

Figure 1:
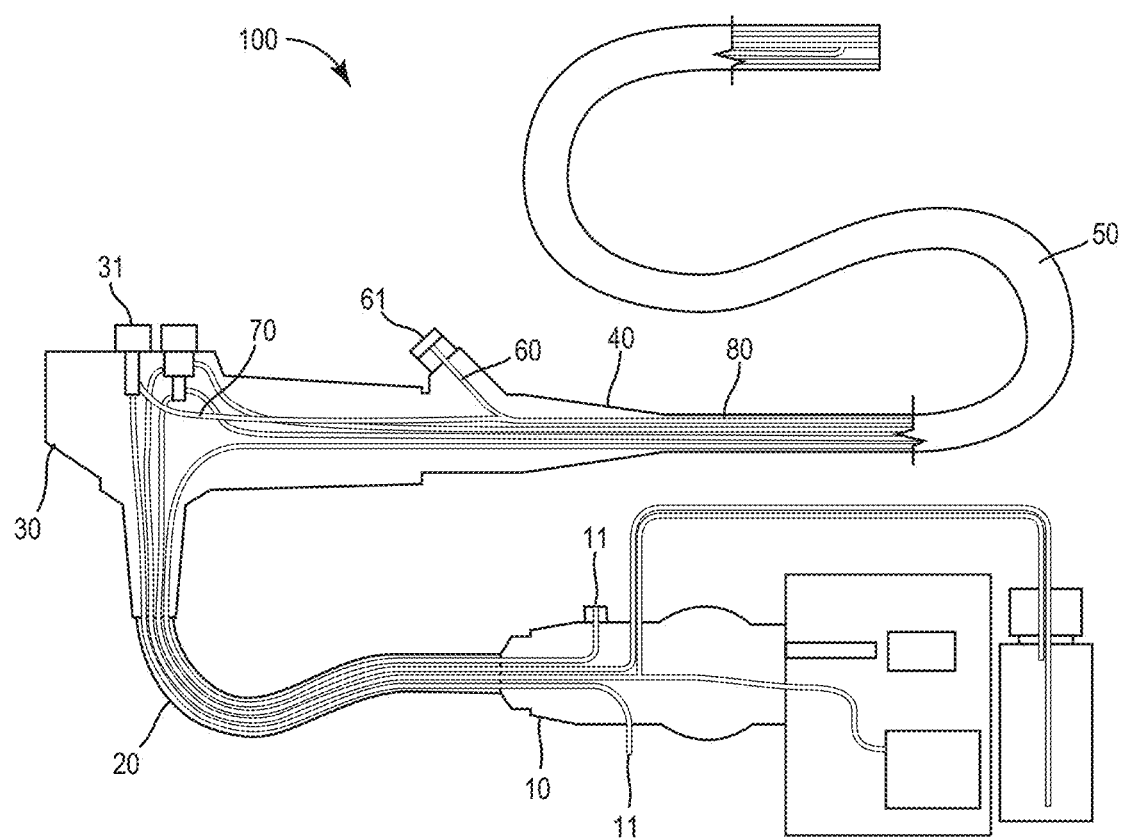
FIG. 1 is a schematic illustration of the parts of an endoscope.
Figure 3:
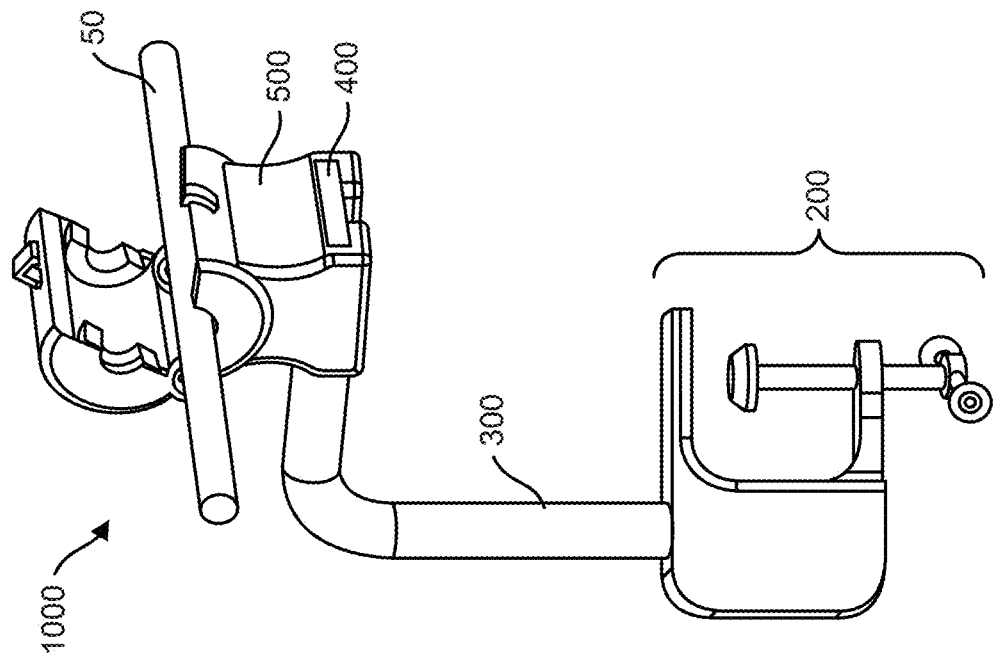
FIG. 3 illustrates the endoscope restraining system of FIG. 2 from another perspective.
Figure 2:
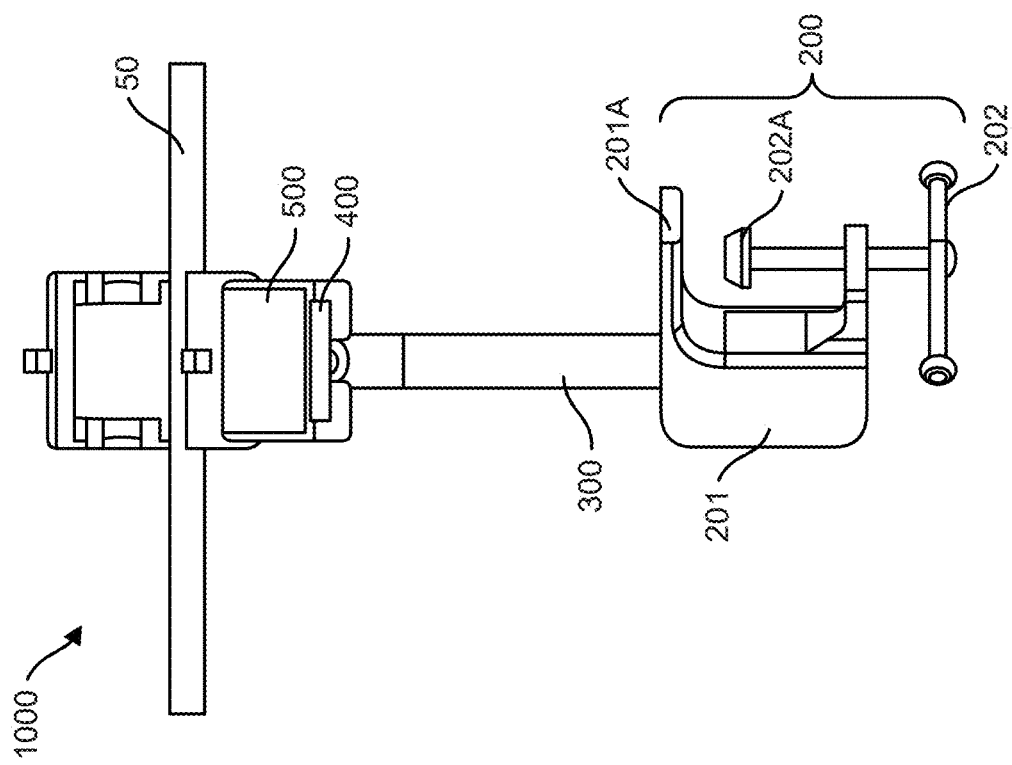
FIG. 2 illustrates an endoscope restraining system.
Figure 5:
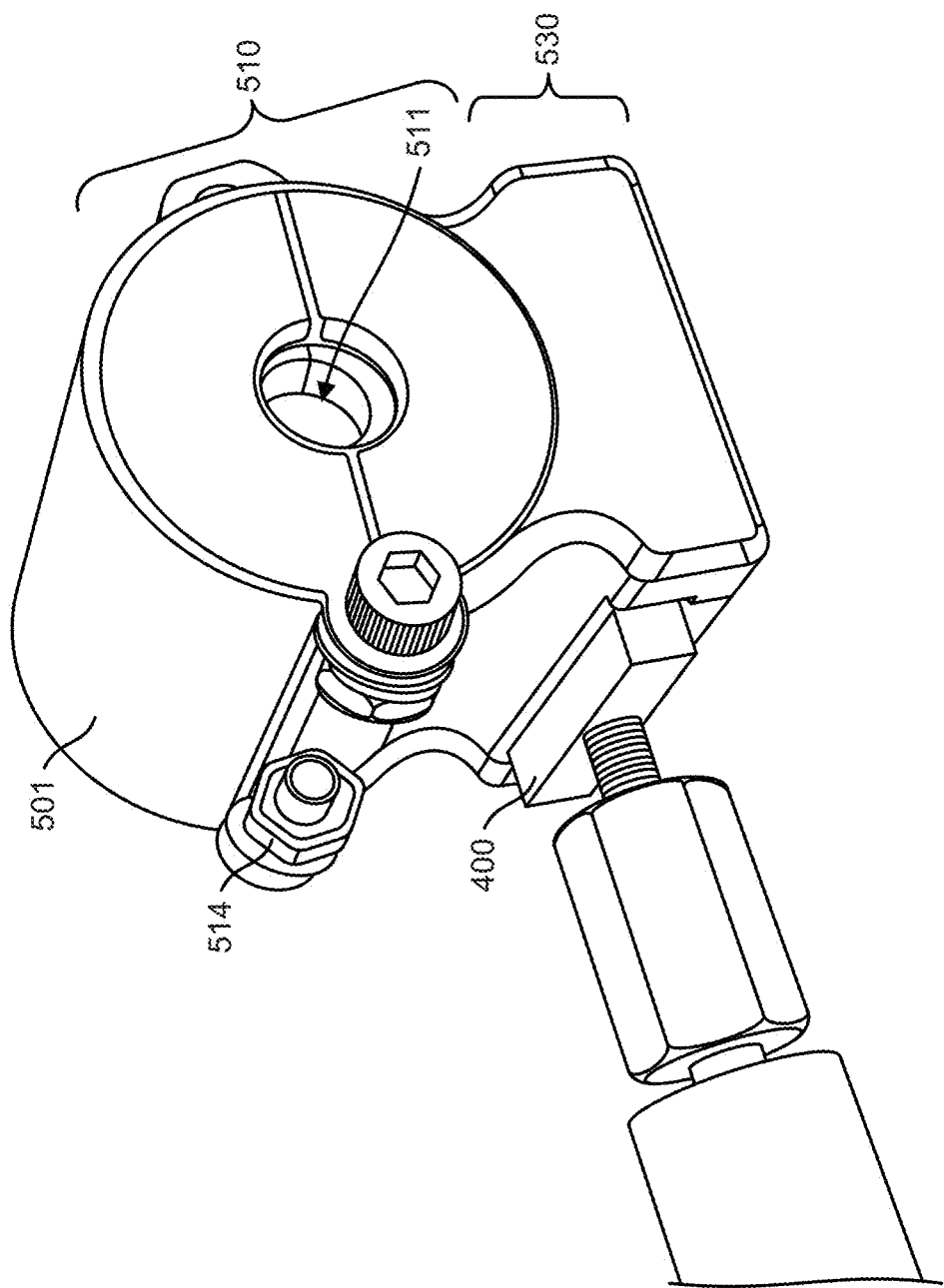
FIG. 5 illustrates a view of an endoscope restraint of the endoscope restraining system of FIG. 4 in a closed position.
Figure 6:
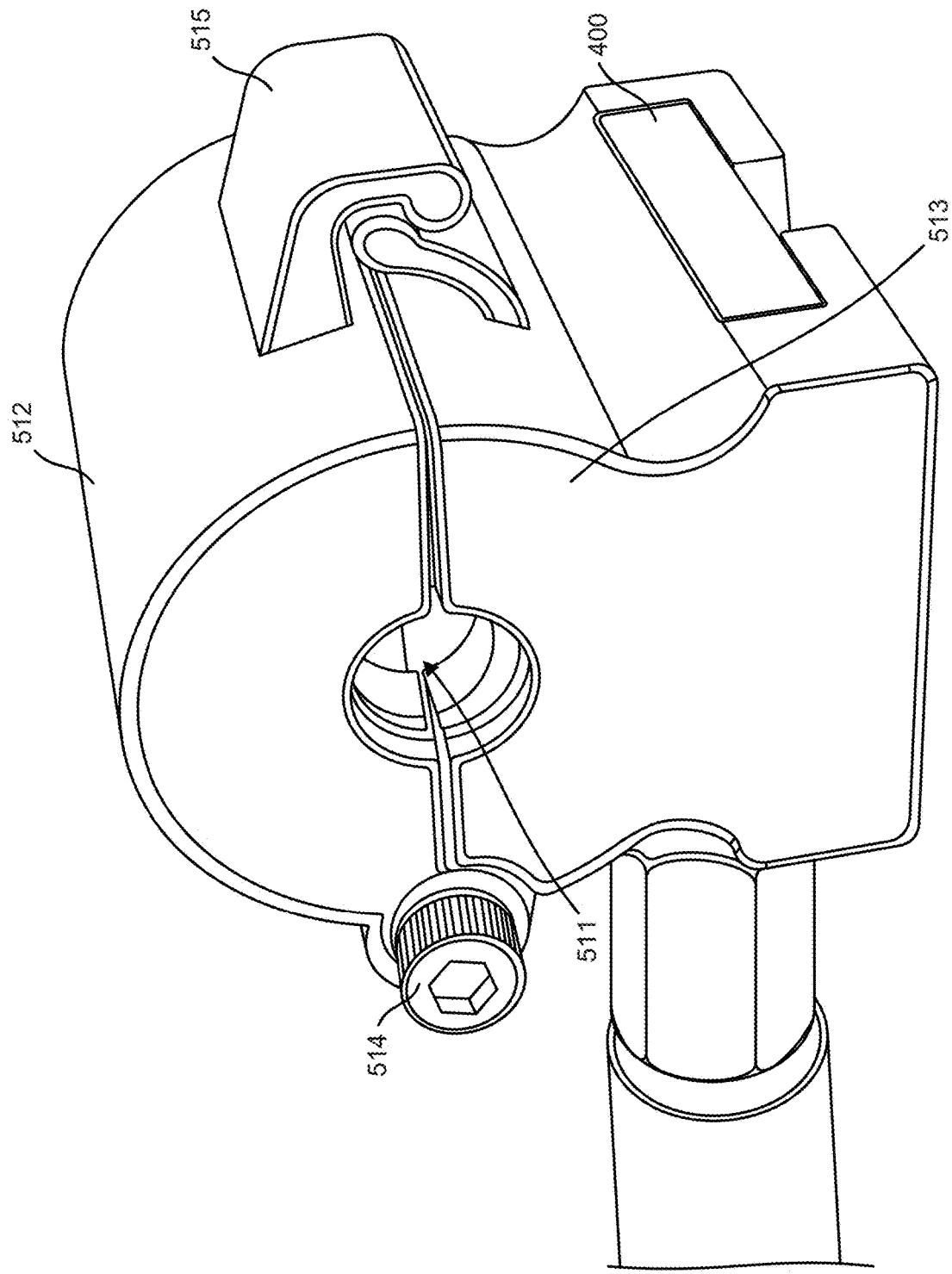
FIG. 6 illustrates the endoscope restraint of FIG. 5 from another perspective.

Before turning to the figures, which illustrate the exemplary embodiments in detail, it should be understood that the present application is not limited to the details or methodology set forth in the description or illustrated in the figures. It should also be understood that the terminology is for the purpose of description only and should not be regarded as limiting.

Referring now to FIGS. 2-23, an endoscope restraining system 1000 for restraining the motion of an endoscope tube 50 includes an attachment portion 200 configured to attach the endoscope restraining system 1000 to a surface (e.g., table, bed, bed frame, other flat surface or other curved surface), a flexible tube 300 coupled to the attachment portion 200 at a proximal end of the flexible tube 300, a base plate 400 coupled to a distal end of the flexible tube 300, and an endoscope restraint 500 removably connected to the base plate 400. As described in further detail below, the endoscope restraint 500 is configured to receive the endoscope tube 50 in a bore 511 thereof to prevent changes in a torque position (clockwise/counterclockwise direction), degree of insertion (forward/backwards direction), and lateral movement of the endoscope tube 50.

The attachment portion 200 may be, for example, any type of clamp or clip capable of attaching the endoscope restraining system 1000 to the surface. In one example, the attachment portion 200 is a C clamp (also known as a G clamp) having a C-shaped frame 201 and an adjustable screw 202 that can be reversibly tightened to provide a desired force to secure the surface between a flat end 201A of the C-shaped frame 201 and a flat end 202A of the adjustable screw 202. In other examples, the attachment portion 200 may be a bed clamp, a screw clamp, a power clamp, a spring clamp, etc., provided that the attachment portion 200 is capable of attaching the endoscope restraining system 1000 to a table, bed, or other flat surface, or to a curved surface such as a bed frame.

As seen in FIG. 4, the flexible tube 300 is coupled to the attachment portion 200. The flexible tube 300 is configured to support the weight of the base plate 400, the endoscope restraint 500 and the endoscope tube 50 while maintaining its position. When desired, the position of the flexible tube 300 may be manually adjusted by the endoscopist by applying pressure to the flexible tube 300. The flexible tube 300 may be, for example, an elephant trunk tube, a flexible steel conduit, a gooseneck, a flexible metal tubing, a flexible house, a corrugated metal tube, or a corrugated metal tube having an elastomeric outer sheathing. The flexible tube 300 can be bent and adjusted in all directions and all angles (i.e. 360 degrees) to change a height or position of the endoscope restraint 500. For example, in operation of the endoscope restraint 500, the flexible tube 300 may be bent such that the base plate 400 is parallel with the surface to which the endoscope restraint 500 is secured (see FIG. 4), such that the base plate 400 is perpendicular with the surface to which the endoscope restraint is secured (see FIG. 23), or such that the base plate 400 is provided at any position or angle between the parallel and perpendicular positions illustrated in FIGS. 4 and 23, respectively.

The base plate 400 is removably coupled to a distal end of the flexible tube 300. In one example, the base plate 400 includes a screw 405 attached at a proximal end thereof, which connects to the flexible tube 300 via a screw adapter 410 (see FIGS. 16 and 17). The screw adapter 410 may be, for example, a hex nut. The base plate 400 may be quick released in order to sanitize/sterilize the base plate 400, for example, in an autoclave. Provision of the screw adapter 410 allows the base plate 400 to be removed often for cleaning and/or sterilization without causing the threads of the flexible tube 300 to wear. In other words, using the intermediate screw adapter 410 may ensure that the threads of the flexible tube 300 (often more expensive than the base plate 400) is protected from wear due to daily use and repeated attachment/removal of the base plate 400.

The base plate 400 is made of any biomaterial. For example, the base plate may be made of surgical grade steel, cobalt-chrome steel, stainless steel, and/or titanium. The base plate may also be made of plastic. In one example, the base plate is approximately 1.5 inches wide, 2 inches long, and 0.25 inches thick. The base plate 400 is made from a material that can be easily wiping and sanitized/sterilized.

The endoscope restraint 500 removably connected to the base plate 400. As best illustrated in FIGS. 5-10, the endoscope restraint 500 is comprised of a housing 501 having an endoscope tube retention portion 510 and a base plate retention portion 530, where the endoscope tube retention portion 510 and the base plate retention portion 530 are integrally formed. The housing 501 may be formed, for example, by 3D printing, injection molding, casting, sheet molding or stamping. As illustrated, the housing 501 has a keyhole shape, but the invention is not limited in this regard.

The endoscope tube retention portion 510 includes a bore 511 defined by an opening in side walls of the endoscope tube retention portion 510 and a plurality of supports 520 provided within the endoscope tube retention portion 510. The bore 511 extends through an entire length of the endoscope tube retention portion 510. The endoscope tube 50 is configured to be received in the bore 511.

The housing 501 is divided into an upper half 512 and a lower half 513 that are hinged to each other about a longitudinal axis of the endoscope tube retention portion 510 via a hinge 514. The hinge 514 may be, for example, a screw or pin. The upper half 512 is rotatable with respect to the lower half 513 about the hinge 514 such that the endoscope tube retention portion 510 may be in an open position in which a torque position (clockwise/counterclockwise direction), degree of insertion (forward/backwards direction), and lateral movement of the endoscope tube 50 can be adjusted, or a closed position in which position the torque position (clockwise/counterclockwise direction), degree of insertion (forward/backwards direction), and lateral movement of the endoscope tube 50 is locked. In the closed position, the rotation of the upper half 512 with respect to the lower half 513 is locked by a rotation locking mechanism 515 that secures the upper half 512 to the lower half 513. The rotation locking mechanism 515 may be, for example, at least one latch. In a preferred embodiment, the rotation locking mechanism can be locked and released with one finger to allow the endoscopist to easily adjust a torque position, degree of insertion or lateral movement of the endoscope tube 50 during a procedure.

An interior of the endoscope tube retention portion 510 includes a plurality of supports 520. One support may be unable to restrain the endoscope tube 50 to prevent changes in the torque position (clockwise/counterclockwise direction) thereof. As illustrated, the endoscope tube retention portion 510 includes two supports 520. As seen in FIGS. 7-10, each of the two supports 520 is provided proximate to an opening in a side wall of the endoscope tube retention portion 510. The two supports 520 are provided, for example, approximately 1 to 1.5 inches apart. Although more than two supports 520 may be provided, the introduction of more supports may induce bending in the endoscope tube 50 if there is any mismatch in the height of the supports. Such bending can reduce the life of the endoscope. In examples using two supports 520, the two supports 520 are always connected by a straight line, eliminating the possibility of inducing bending by the supports 520.

In some embodiments, gap 521 is provided between the side wall of the endoscope tube retention portion 510 and the support 520. The gap 521 is configured to capture any excess lubricant provided on the endoscope tube 50. In one example, the gap 521 may be in a range of 1-2 mm.

Each support 520 is divided into an upper portion 522 that is fixed to the upper half 512 of the housing 501 and a lower portion 523 that is fixed to the lower half 513 of the housing 501. In some embodiments, the upper portion 522 and the lower portion 523 of the support 520 are mirror-symmetrical around longitudinal axis of the endoscope tube retention portion 510. A surface of the upper portion 522 that faces the lower portion 523 includes a semicircular groove 522A. A surface of the lower portion 523 that faces the upper portion 522 includes a semicircular groove 523A.

The semicircular groove 522A and the semicircular groove 523A of each support 520 is lined a layer 524 configured to grip the endoscope tube 50 without causing severe stress concentration at the location of the grip. The layer 524 may be comprised, for example, of silicone or polydimethylsiloxane (PDMS). Finite element analysis was conducted on the endoscope restraining system 1000 by assuming a small bending displacement on the endoscope tube 50 at the center between the two supports 520 to calculate the effect of bending stress with respect to the stiffness of a silicone layer 524. A model set of analysis parameters is shown in Table 2.

TABLE 2

Material Properties

| | Density (g/cm$^3$) | Young's Modulus (MPa) | Geometry Parts |
|---|---|---|---|
| ABS Plastic | 1.04 | 3091.7 | Main Support |
| Polyvinyl Chloride | 1.4 | 1400 | Endoscopy Tube |
| Silicone Rubber | 1.1 | 1 | Silicone Layers |

Properties of other materials can also be taken as inputs in this analysis based on the choice of materials. Table 3 shows geometrical parameters used in a model set of analysis for induced 0.01 m displacement.

TABLE 3

Stress Concentrations and Distance Between Two Supports

| Model | Distance between two supports (inches) | Endoscope displacement (m) | Endoscopy tube stress (MPa) | Main support stress (MPa) |
| --- | --- | --- | --- | --- |
| 1 | 7 | 0.01 | 32.3 | 4.5 |
| 2 | 5 | 0.01 | 60.0 | 7.3 |
| 3 | 4 | 0.01 | 136.4 | 12.3 |

Figure 20:
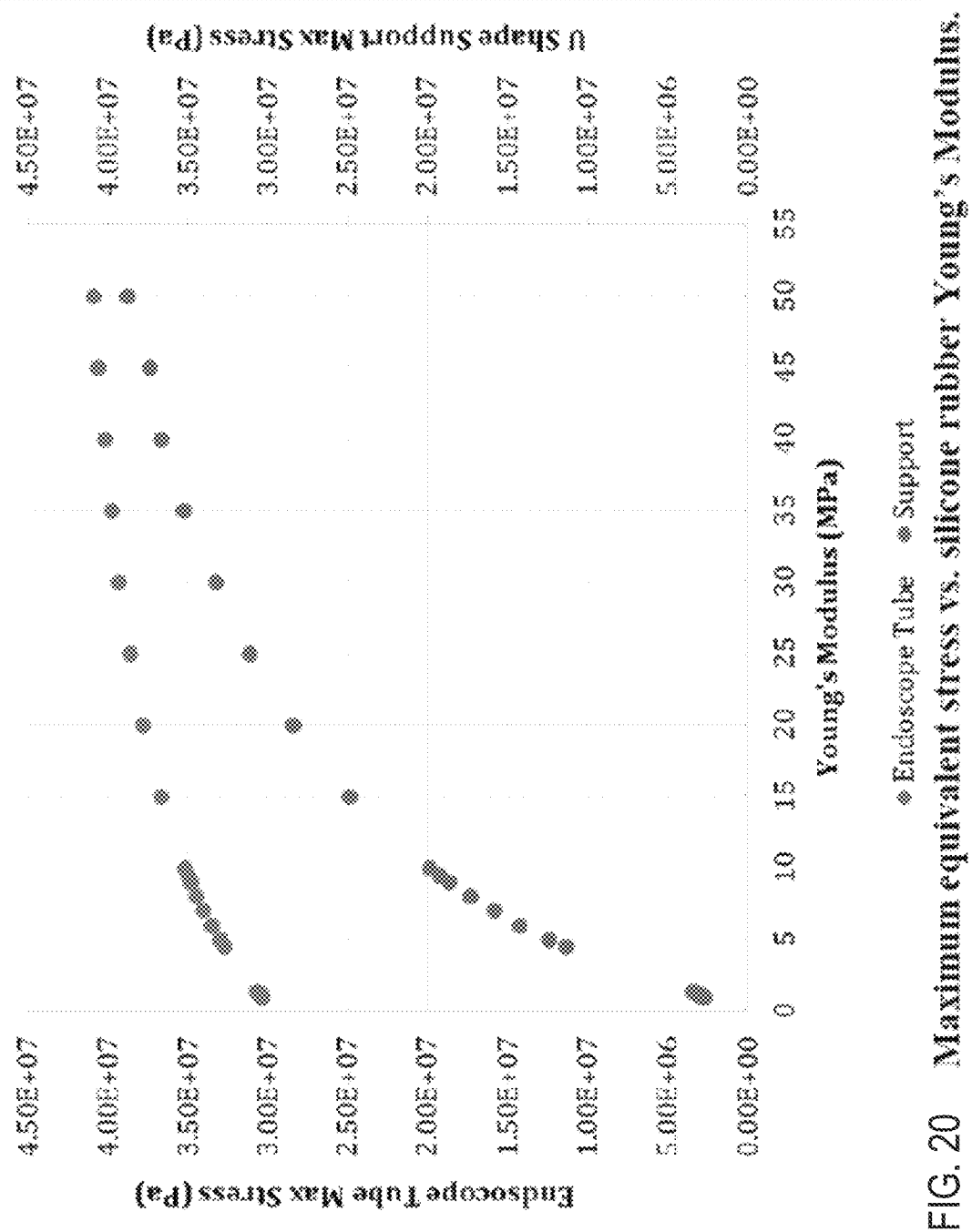
FIG. 20 is a graph depicting a maximum equivalent stress versus Young's modulus of a silicone layer that lines a support of an endoscope restraint.
Figure 21:
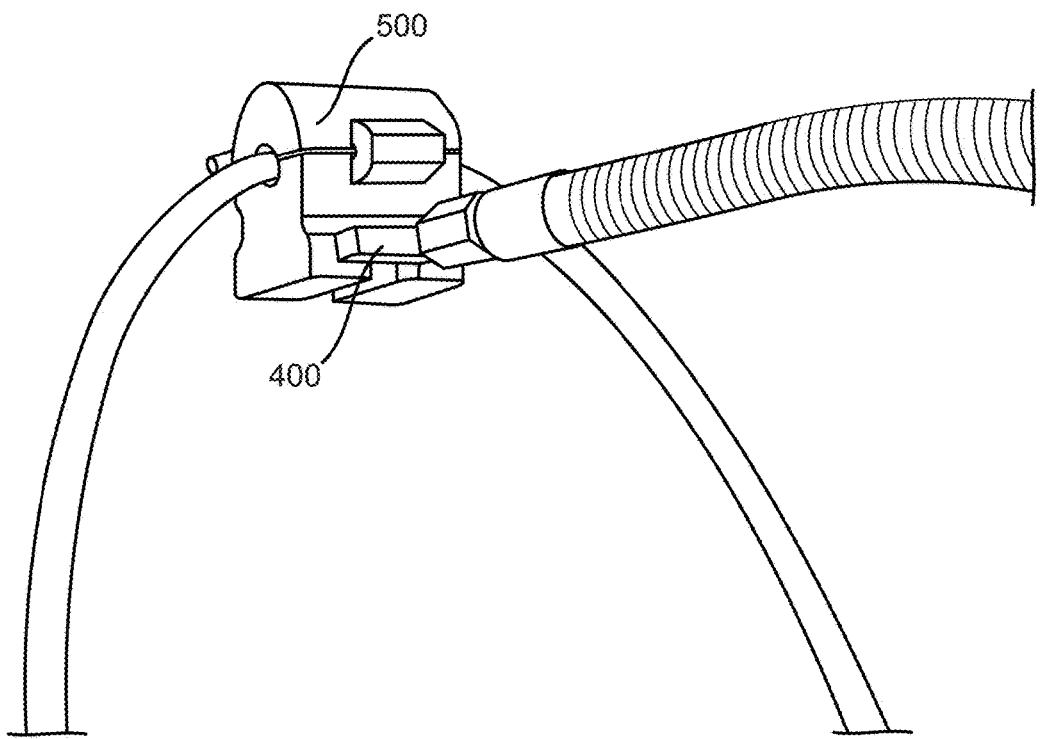
FIG. 21 illustrates the endoscope restraining system of FIG. 2 in which an endoscope restraint is supported above a base plate.
Figure 22:
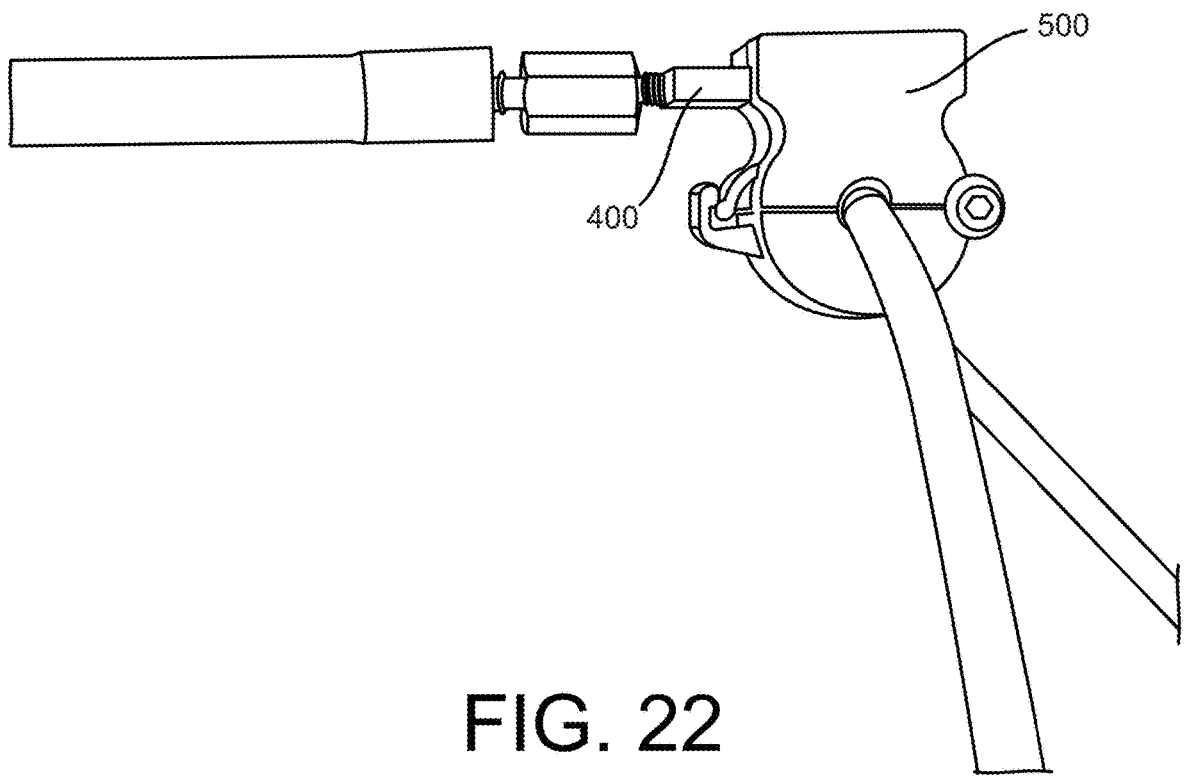
FIG. 22 illustrates the endoscope restraining system of FIG. 2 in which an endoscope restraint is supported below a base plate.
Figure 23:
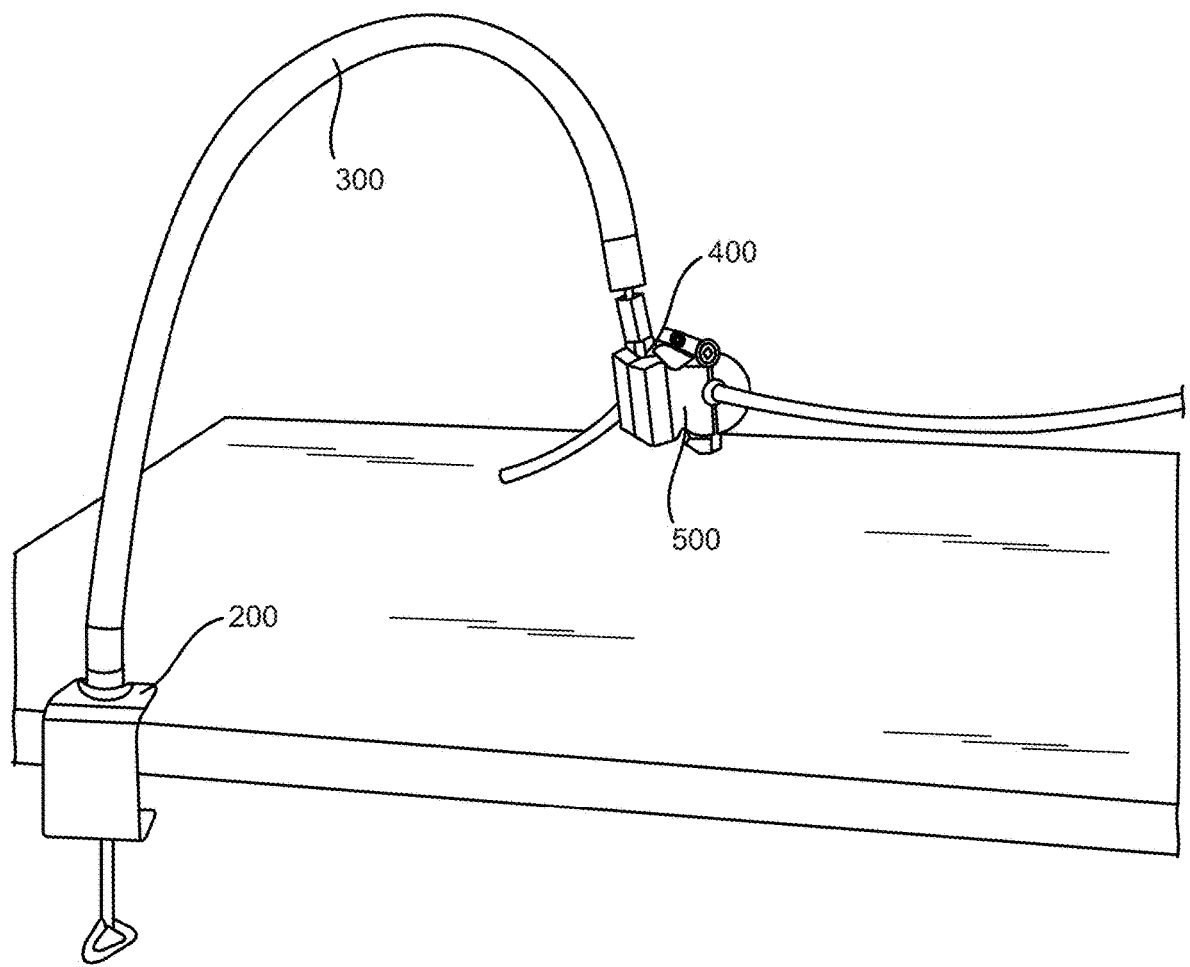
FIG. 23 illustrates the endoscope restraining system of FIG. 2 where a flexible tube of the endoscope restraining system is bent such that a base plate of the endoscope restraining system is perpendicular to a surface to the table.

Other analysis parameters can be selected. However, the general trend observed in FIG. 20 is expected to be similar with different absolute values. Based on the analysis, in one embodiment of the invention, silicone with a Young's modulus of 30 MPa and of 1 mm layer thickness was selected as the layer 524. In other embodiments, the Young's modulus of the layer 524 may be from 10-70 MPa, with the thickness varied accordingly. One of ordinary skill in the art would appreciate that a lower Young's modulus will require a higher thickness.

The advantage of using silicone as the layer 524 is that the high surface shear provided by electrostatic forces of silicon provides adhesive action with the endoscope tube 50 to reduce the torsional motion. Due to numerous unsaturated bonds in engineered silicones, silicones are able to bond with a substrate without any adhesive. The shear strength of such bonded silicones can be very high, while the silicone can still peel off easily. Porous layers of silicone or the other selected layer material can also be useful because the layer 524 can absorb the lubricant from the surface of the endoscope tube 50 and further restrict the motion. The silicone layer 524 also squeezes the surface of the endoscope tube 50 (without bending the endoscope tube 50) to provide a cleaning action that displaces the lubricant and helps in obtaining grip to restrict rotational movement of the endoscope.

When the endoscope tube retention portion 510 is in the closed position, the semicircular groove 522A and the semicircular groove 523A form a circle having the same diameter as the bore 511. The diameter of the bore 511 is selected based on the diameter of the endoscope tube 50.

Figure 7:
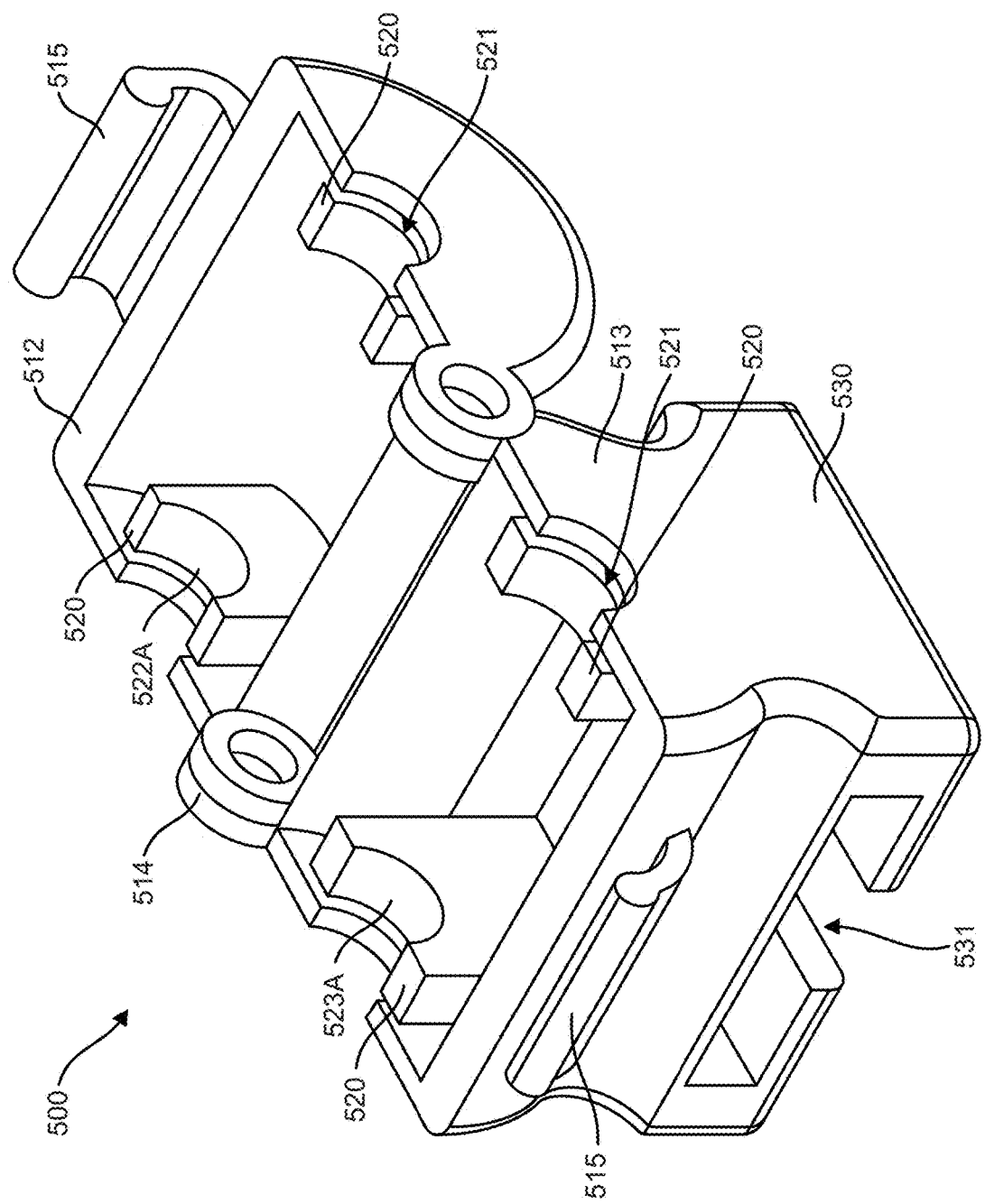
FIG. 7 illustrates a view of an endoscope restraint of the endoscope restraining system of FIG. 4 in an open position.
Figure 8:
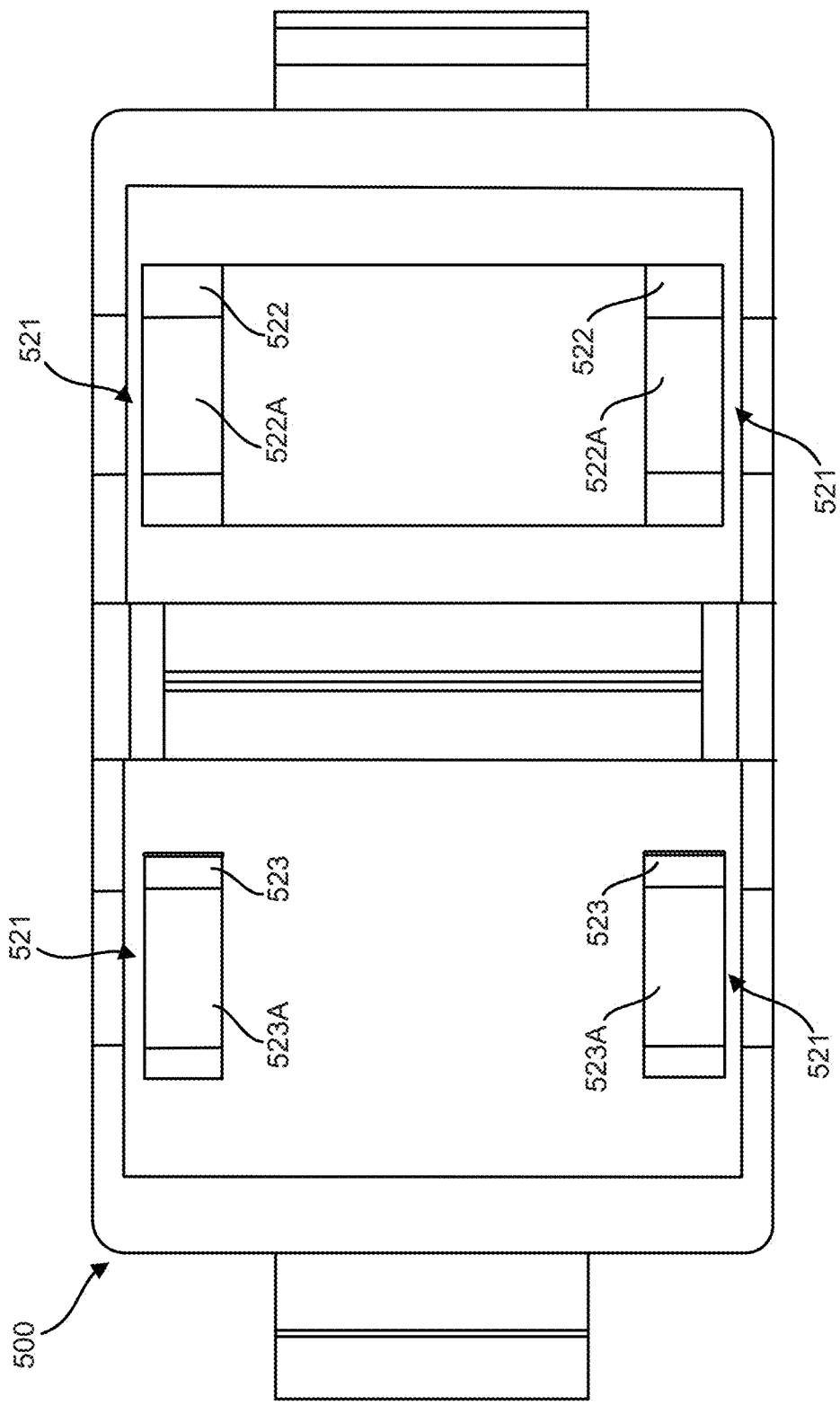
FIG. 8 illustrates a top view of the endoscope restraint of FIG. 7.
Figure 9:
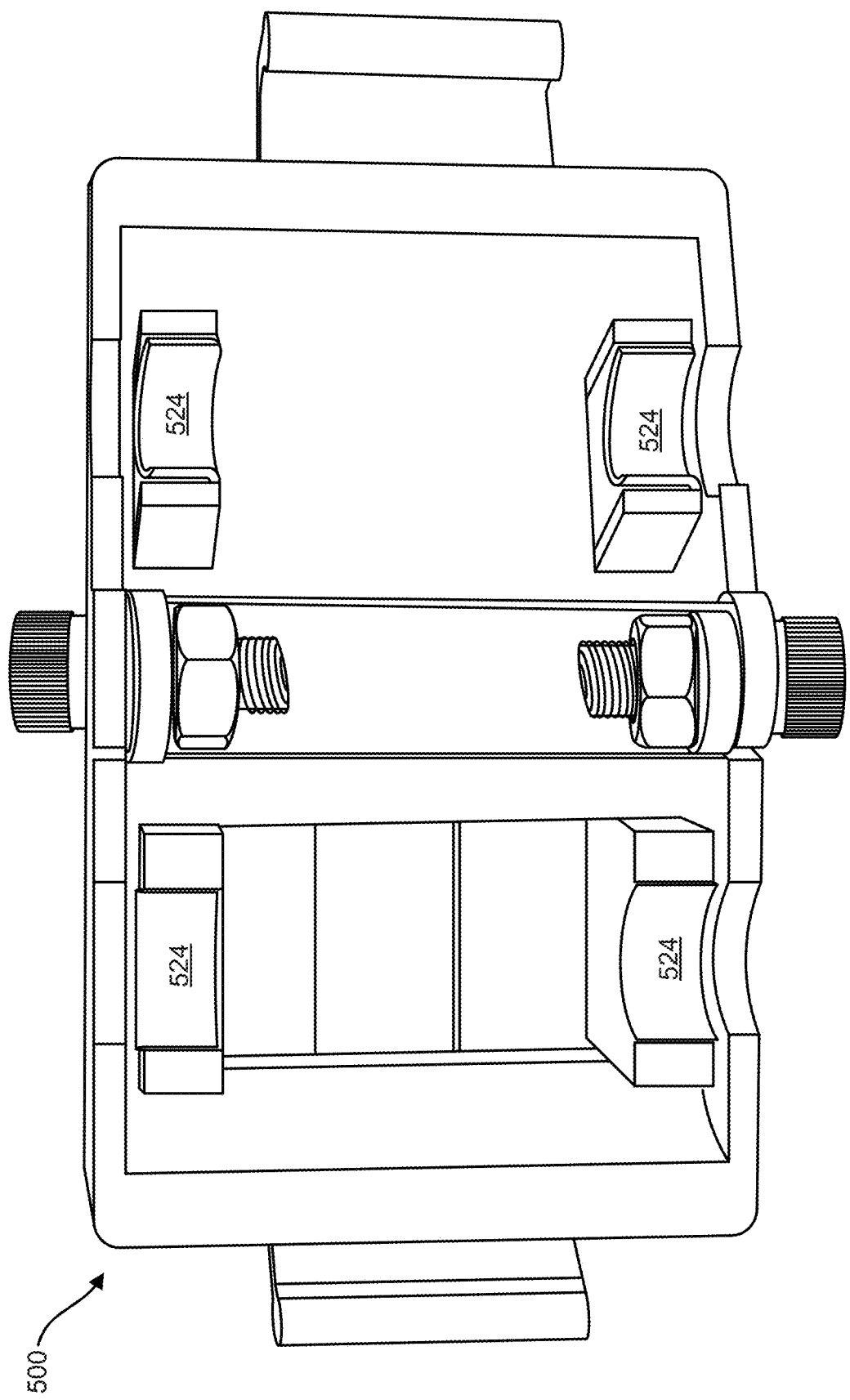
FIG. 9 illustrates another top view of the endoscope restraint of FIG. 7.
Figure 15:
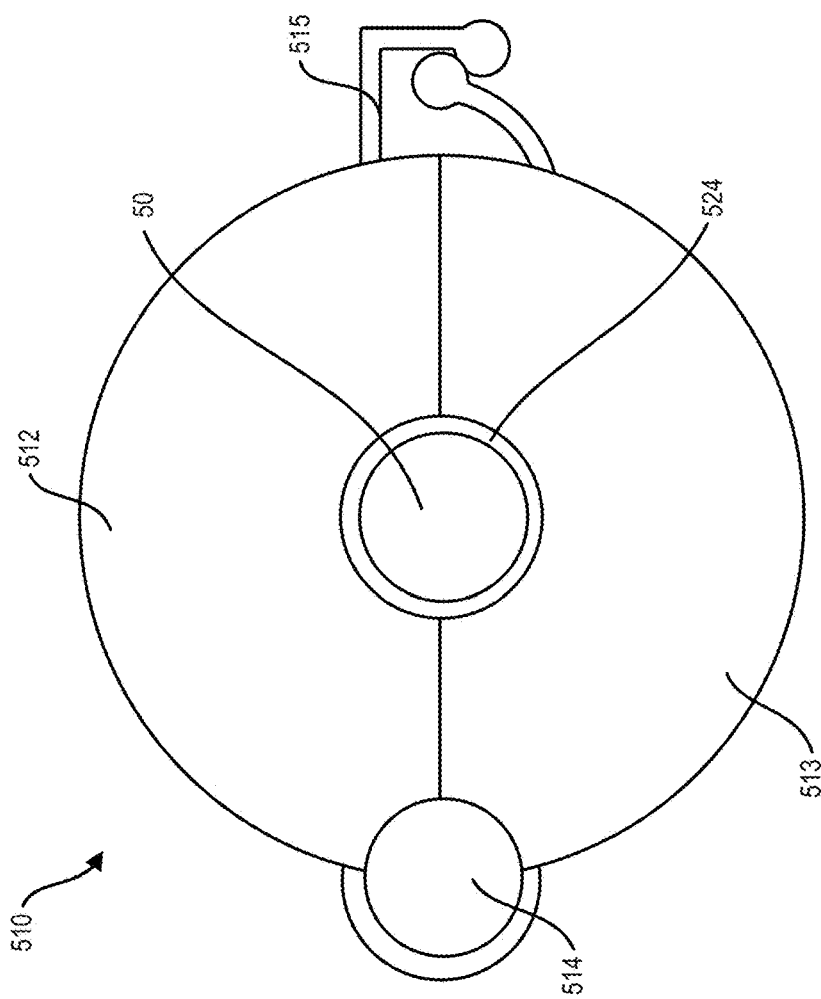
FIG. 15 illustrates a side view of the endoscope restraint of FIG. 5.
Figure 14:
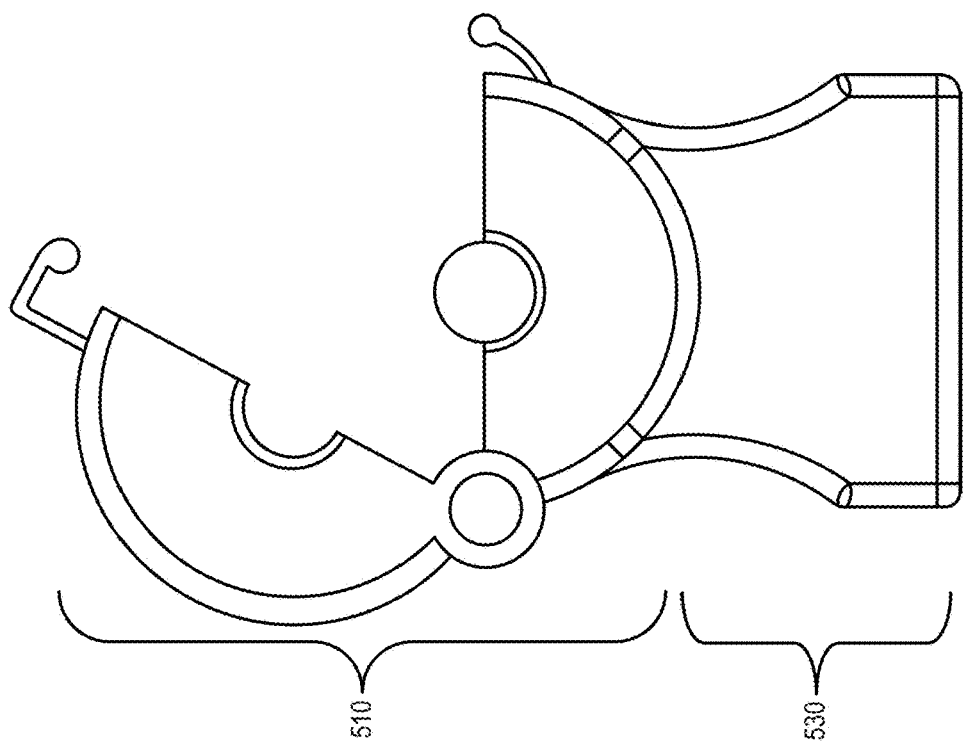
FIG. 14 illustrates a side view of the endoscope restraint of FIG. 7.
Figure 16:
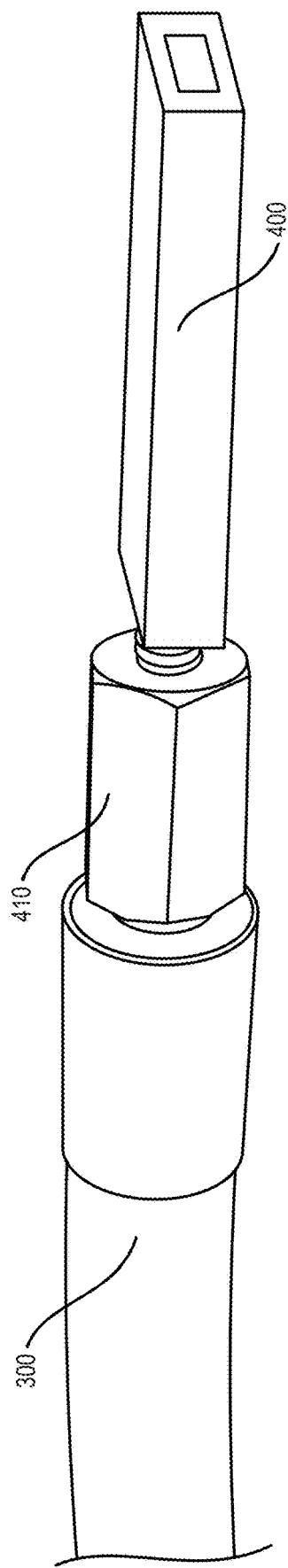
FIG. 16 illustrates a flexible tube and a base plate of the endoscope restraining system of FIG. 2.
Figure 17:
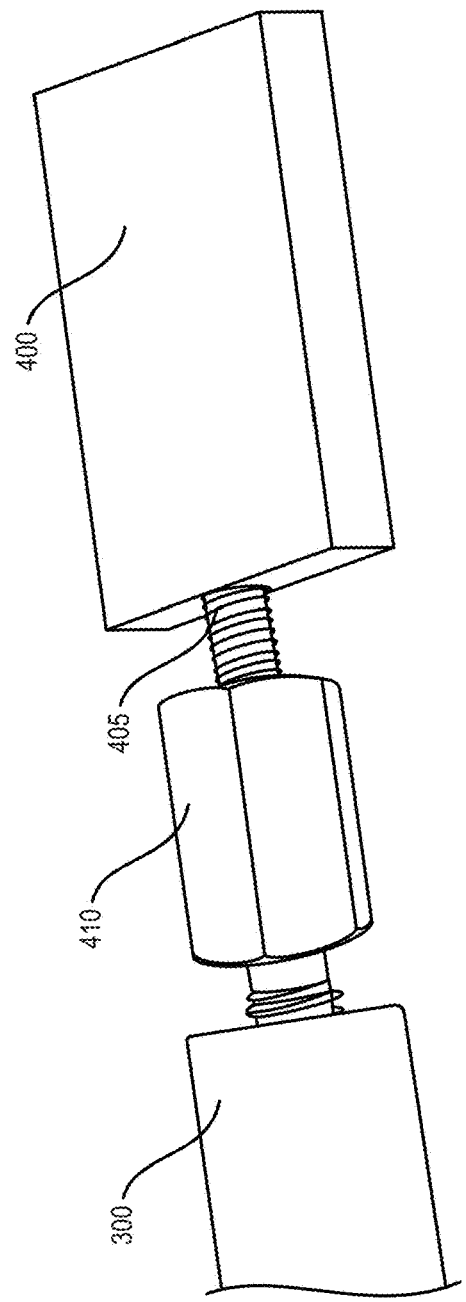
FIG. 17 illustrates a screw and a screw adapter connecting the flexible tube and the base plate of FIG. 16.
Figure 18:
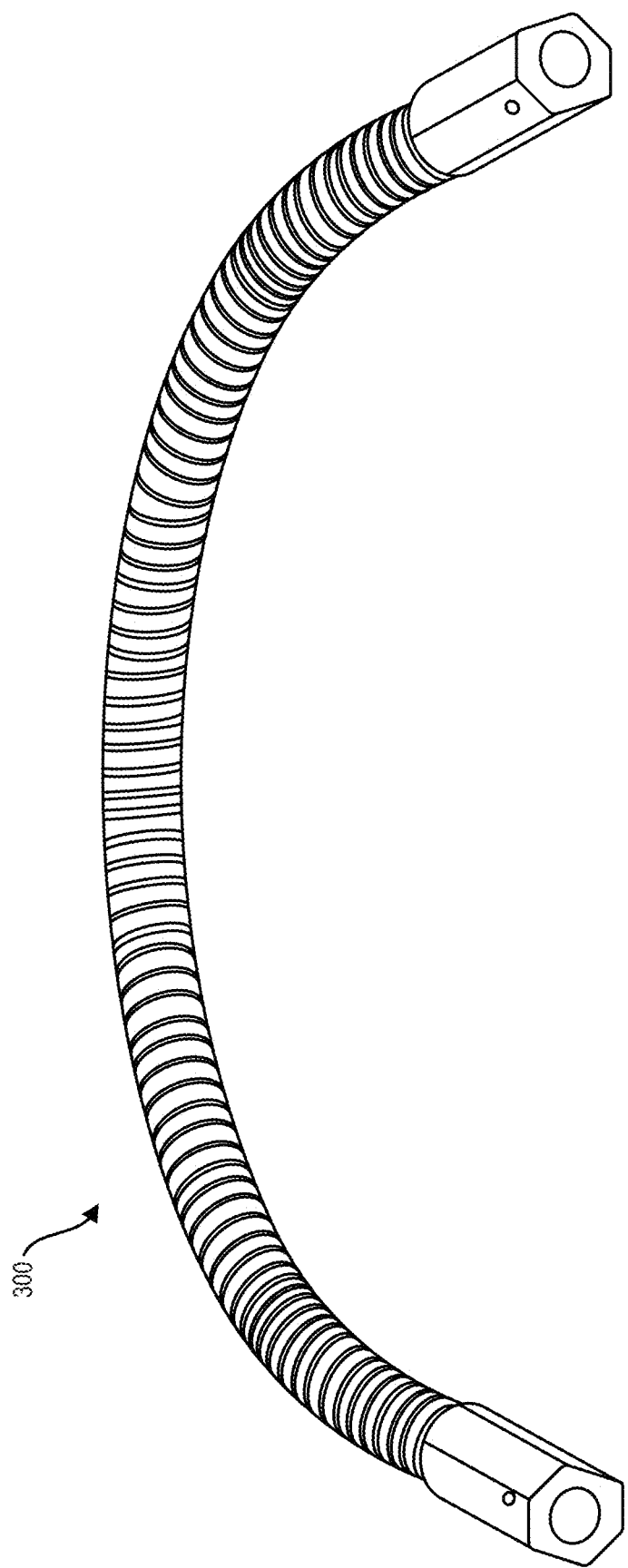
FIG. 18 illustrates a flexible tube of the endoscope restraining system of FIG. 2.
Figure 19:
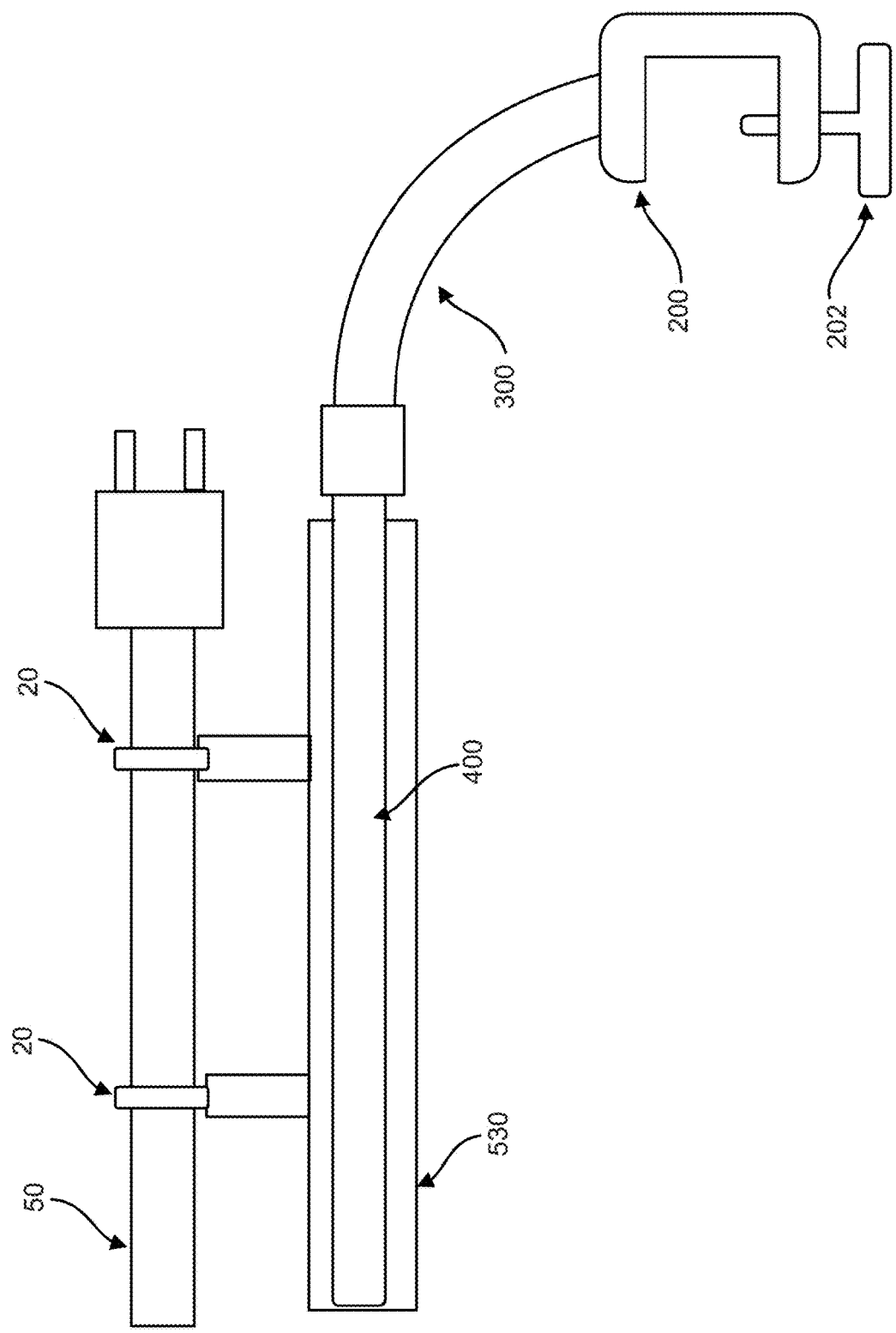
FIG. 19 is a schematic illustration of the endoscope restraining system of FIG. 2 with the housing of the endoscope restraint removed to illustrate the plurality of supports.

In some embodiments, such as shown in FIG. 7, the base plate retention portion 530 includes a rectangular slot 531 configured to receive the base plate 400 and secure the endoscope restraint 500 to the base plate 400 via friction fit. The slot 531 extends in a direction perpendicular to the longitudinal axis of the endoscope tube retention portion 510. The base plate retention portion 530 is configured to be slide over the base plate 400 to removably connect the endoscope restraint 500 to the base plate 400. The slot 531 may be sized and dimensioned to mate with the base plate 400 via friction fit. The slot 531 may mate with the base plate 400 such that the endoscope restraint 500 is supported above (i.e., on top of) the base plate 400 (see FIG. 21) or such that the endoscope restraint 500 is supported below the base plate 400 (see FIG. 22).

In one example, the endoscope restraint 500 is disposable and configured for single use. In such an example, the housing 501 and the supports 520 can be made of any plastic suitable for medical use, for example, high density polyethylene, polyactic acid (PLA), or acrylonitrile butadiene styrene (ABS).

In one example, the endoscope restraint 500 is reusable and formed of a material that can be easily sanitized/sterilized, for example, via autoclave. In such an example, the housing 501 and the supports 520 can be made of metal. The metal can be, for example, surgical grade steel or titanium.

The endoscope retraining system 1000 eliminates the need for having two people stabilize and operate the endoscope during a procedure. Using the endoscope restraining system 1000, an endoscopist can easily lock the endoscope tube 50 in position after locating a polyp, thus eliminating the need of transition to a nurse or technician to hold torque while the endoscopist removes the polyp. This ensures that the location of the polyp is not lost, for example, due to the torque which the nurse or technician provides not matching that previously provided by the endoscopist to hold the endoscope tube in position.

The construction and arrangements of the endoscope restraining system, as shown in the various exemplary embodiments, are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, image processing and segmentation algorithms, etc.) without materially departing from the novel teachings and advantages of the subject matter described herein. Some elements shown as integrally formed may be constructed of multiple parts or elements, the position of elements may be reversed or otherwise varied, and the nature or number of discrete elements or positions may be altered or varied. The order or sequence of any process, logical algorithm, or method steps may be varied or re-sequenced according to alternative embodiments. Other substitutions, modifications, changes and omissions may also be made in the design, operating conditions and arrangement of the various exemplary embodiments without departing from the scope of the present invention.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

The terms "coupled," "connected," and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

References herein to the positions of elements (e.g., "top," "bottom," "above," "below," etc.) are merely used to describe the orientation of various elements in the FIGURES. It should be noted that the orientation of various elements may differ according to other exemplary embodiments, and that such variations are intended to be encompassed by the present disclosure.

With respect to the use of substantially any plural and/or singular terms herein, those having skill in the art can translate from the plural to the singular and/or from the singular to the plural as is appropriate to the context and/or application. The various singular/plural permutations may be expressly set forth herein for the sake of clarity.

What is claimed is:

1. An endoscope restraining system for restraining motion of an endoscope tube, the endoscope restraining system comprising:
    an attachment portion configured to attach the endoscope restraining system to a surface;
    a flexible tube coupled to the attachment portion at a proximal end of the flexible tube;
    a base plate coupled to a distal end of the flexible tube; and
    an endoscope restraint removably connected to the base plate, the endoscope restraint comprising a housing having an upper half and a lower half that are hinged to each other to allow the upper half to rotate with respect to the lower half, the housing configured to receive the endoscope tube between the upper half and the lower half, the housing further including a plurality of supports that includes at least two supports disposed within the housing, each of the at least two supports having an upper portion fixed to the upper half and having an upper portion semicircular groove and a lower portion fixed to the lower half and having a lower portion semicircular groove, the plurality of supports configured to receive the endoscope tube within the upper portion semicircular groove and the lower portion semicircular groove to prevent changes in a torque position, degree of insertion, and lateral movement of the endoscope tube.

2. The endoscope restraining system of claim 1, wherein the housing of the endoscope restraint is configured between an open position in which the torque position, degree of insertion, and lateral movement of the endoscope tube is adjustable, and a closed position in which the torque position, degree of insertion, and lateral movement of the endoscope tube is locked and further wherein the upper portion semicircular groove and lower portion semicircular groove form a circular passage when the housing is in the closed position.

3. The endoscope restraining system of claim 2, further comprising a rotation locking mechanism configured to secure the upper half to the lower half when the endoscope restraint is in the closed position.

4. The endoscope restraining system of claim 3, wherein the rotation locking mechanism comprises at least one latch.

5. The endoscope restraining system of claim 1, wherein each of the supports is lined with a layer configured to grip the endoscope tube without causing severe stress concentration at a gripping location.

6. The endoscope restraining system of claim 5, wherein the layer is comprised of silicone.

7. The endoscope restraining system of claim 1, wherein the endoscope restraint is formed of plastic and is configured to be disposed after a single use.

8. The endoscope restraining system of claim 1, wherein the endoscope restraint is formed of metal and is configured to be reused after sterilization.

9. An endoscope restraint for an endoscope tube, the endoscope restraint comprising:
    a housing including an endoscope tube retention portion and a base plate retention portion,
    wherein the endoscope tube retention portion is divided into an upper half and a lower half that are hinged to each other to allow the upper half to rotate with respect to the lower half, the endoscope tube retention portion configured to receive the endoscope tube between the upper half and the lower half, the endoscope tube retention portion further includes a plurality of supports that include at least two supports disposed within the housing, each of the at least two supports having an upper portion fixed to the upper half and having an upper portion semicircular groove and a lower portion fixed to the lower half and having a lower portion semicircular groove, the plurality of supports configured to receive an endoscope tube to prevent changes in a torque position, degree of insertion, and lateral movement of the endoscope tube.

10. The endoscope restraint of claim 9, wherein the endoscope tube retention portion is configured between an open position in which the torque position, degree of insertion, and lateral movement of the endoscope tube is adjustable, and a closed position in which the torque position, degree of insertion, and lateral movement of the endoscope tube is locked.

11. The endoscope restraint of claim 10, wherein the endoscope tube retention portion further comprises a rotation locking mechanism configured to secure the upper half to the lower half when the endoscope restraint is in the closed position.

12. The endoscope restraint of claim 11, wherein the rotation locking mechanism comprises at least one latch.

13. The endoscope restraint of claim 9, wherein each of the supports is lined with a layer configured to grip the endoscope tube without causing severe stress concentration at a gripping location.

14. The endoscope restraint of claim 9, wherein the endoscope restraint is formed of plastic and is configured to be disposed after a single use.

15. The endoscope restraint of claim 9, wherein the endoscope restraint is formed of metal and is configured to be reused after sterilization.

16. The endoscope restraint of claim 9, wherein the base plate retention portion includes a slot configured to secure to a base plate to hold the endoscope restraint in position.

17. A method of restraining motion of an endoscope tube during a surgical procedure, the method comprising:
    attaching an endoscope restraining system to a surface, the endoscope restraining system including a base plate coupled to a distal end of a flexible tube
    connecting an endoscope restraint to the base plate, the endoscope restraint having an upper half and a lower half that are hinged to each other to allow the upper half to rotate with respect to the lower half; and
    securing the endoscope tube within the upper half and the lower half of the endoscope restraint via a plurality of supports that include at least two supports disposed within the housing, each of the at least two supports having an upper portion fixed to the upper half and having an upper portion semicircular groove and a lower portion fixed to the lower half and having a lower portion semicircular groove, the plurality of supports configured to receive the endoscope tube and prevent changes in a torque position, degree of insertion, and lateral movement of the endoscope tube.

* * * * *